(12) United States Patent
Mehier

(10) Patent No.: US 6,719,738 B2
(45) Date of Patent: Apr. 13, 2004

(54) DEVICE FOR DIRECTLY DELIVERING AN ACTIVE SUBSTANCE WITHIN A CELL TISSUE, MEANS FOR IMPLANTING SAID DEVICE AND APPLIANCES FOR INJECTING ACTIVE SUBSTANCE INTO SAID DEVICE

(76) Inventor: Henri Mehier, 18 Quai Tilsitt, Lyons (FR), F-69002

( * ) Notice: Subject to any disclaimer, the term of this patent is extended or adjusted under 35 U.S.C. 154(b) by 24 days.

(21) Appl. No.: 09/860,054

(22) Filed: May 17, 2001

(65) Prior Publication Data

US 2001/0034503 A1 Oct. 25, 2001

Related U.S. Application Data

(63) Continuation of application No. PCT/FR99/02234, filed on Sep. 21, 1999.

(30) Foreign Application Priority Data

Nov. 17, 1998 (FR) .............................................. 98 14582
Mar. 19, 1999 (FR) .............................................. 99 03624

(51) Int. Cl.⁷ .......................... A61M 25/00; A61M 5/00
(52) U.S. Cl. ...................... 604/264; 604/27; 604/93.01; 604/506; 604/522; 604/28
(58) Field of Search .................... 604/27, 28, 43, 604/44, 48, 500, 506, 68, 264, 93.01, 522, 118, 131, 140, 141, 143, 151, 152, 154, 167.01, 167.02, 523, 540–544, 890.1, 4.01, 403, 6.16

(56) References Cited

U.S. PATENT DOCUMENTS

| | | | | | |
|---|---|---|---|---|---|
| 2,257,369 | A | * | 9/1941 | Davis | .......................... 604/43 |
| 4,377,165 | A | * | 3/1983 | Luther et al. | ............ 128/214.4 |
| 4,391,276 | A | * | 7/1983 | Lazarus et al. | ............. 604/266 |
| 4,445,896 | A | * | 5/1984 | Gianturco | ................... 604/256 |

(List continued on next page.)

FOREIGN PATENT DOCUMENTS

| | | | | |
|---|---|---|---|---|
| GB | 1 567 122 | * | 5/1980 | ............ F16L/11/12 |
| WO | WO/89 02290 | | 3/1989 | |
| WO | WO/96 20022 | | 7/1996 | |
| WO | WO/96 36381 | | 11/1996 | |
| WO | WO/97 18001 | | 5/1997 | |
| WO | WO/00 29055 | | 5/2000 | |

OTHER PUBLICATIONS

Widder, Senyei, Sears; Experimental Methods in Cancer Therapeutics; Journal of Pharmaceutical Sciences; Apr. 1982; vol. 71, No. 4; pp. 379–387.

*Primary Examiner*—Brian L. Casler
*Assistant Examiner*—Jennifer Maynard
(74) *Attorney, Agent, or Firm*—Heslin Rothenberg Farley & Mesiti P.C.; John Pietrangelo

(57) ABSTRACT

The invention concerns a device for directly delivering an active substance within all or part of a human or animal tissue cell, characterized in that it is in the form of a hollow tube (1), whereof the walls in contact with said tissue are provided with perforations (5) and whereof the distal end (2) is sealed, while the proximal end (3) is shaped so as to receive removable closing means, said tube being capable of bearing a pressure of at least 50 bars.

13 Claims, 4 Drawing Sheets

U.S. PATENT DOCUMENTS

| | | | | |
|---|---|---|---|---|
| 4,551,146 A | * | 11/1985 | Rogers | 604/403 |
| 4,803,999 A | * | 2/1989 | Liegner | 600/576 |
| 4,857,062 A | * | 8/1989 | Russell | 604/256 |
| 5,009,637 A | * | 4/1991 | Newman et al. | 604/68 |
| 5,041,094 A | * | 8/1991 | Perego et al. | 604/141 |
| 5,080,654 A | * | 1/1992 | Picha et al. | 604/167.02 |
| 5,199,948 A | * | 4/1993 | McPhee | 604/86 |
| 5,254,094 A | | 10/1993 | Starkey et al. | 604/113 |
| 5,306,250 A | * | 4/1994 | March et al. | 604/104 |
| 5,333,626 A | * | 8/1994 | Morse et al. | 128/898 |
| 5,344,412 A | * | 9/1994 | Wendell et al. | 219/121.71 |
| 5,364,374 A | | 11/1994 | Morrison et al. | 604/272 |
| 5,381,510 A | | 1/1995 | Ford et al. | 392/470 |
| 5,569,197 A | * | 10/1996 | Helmus et al. | 604/96 |
| 5,658,892 A | * | 8/1997 | Flotte et al. | 514/44 |
| 5,683,381 A | * | 11/1997 | Carr et al. | 606/27 |
| 5,690,618 A | * | 11/1997 | Smith et al. | 604/232 |
| 5,694,978 A | * | 12/1997 | Heilmann et al. | 138/89 |
| 5,730,720 A | * | 3/1998 | Sites et al. | 604/27 |
| 5,840,061 A | | 11/1998 | Menne et al. | 604/68 |
| 5,871,462 A | * | 2/1999 | Yoder et al. | 604/22 |
| 5,871,484 A | * | 2/1999 | Spievack et al. | 606/60 |
| 5,957,901 A | * | 9/1999 | Mottola et al. | 604/264 |
| 6,096,001 A | * | 8/2000 | Drasler et al. | 604/22 |
| 6,132,405 A | * | 10/2000 | Nilsson et al. | 604/264 |
| 6,280,434 B1 | * | 8/2001 | Kinoshita et al. | 604/530 |
| 6,296,632 B1 | * | 10/2001 | Luscher et al. | 604/890.1 |
| 6,463,317 B1 | * | 10/2002 | Kucharczyk et al. | 600/411 |

\* cited by examiner

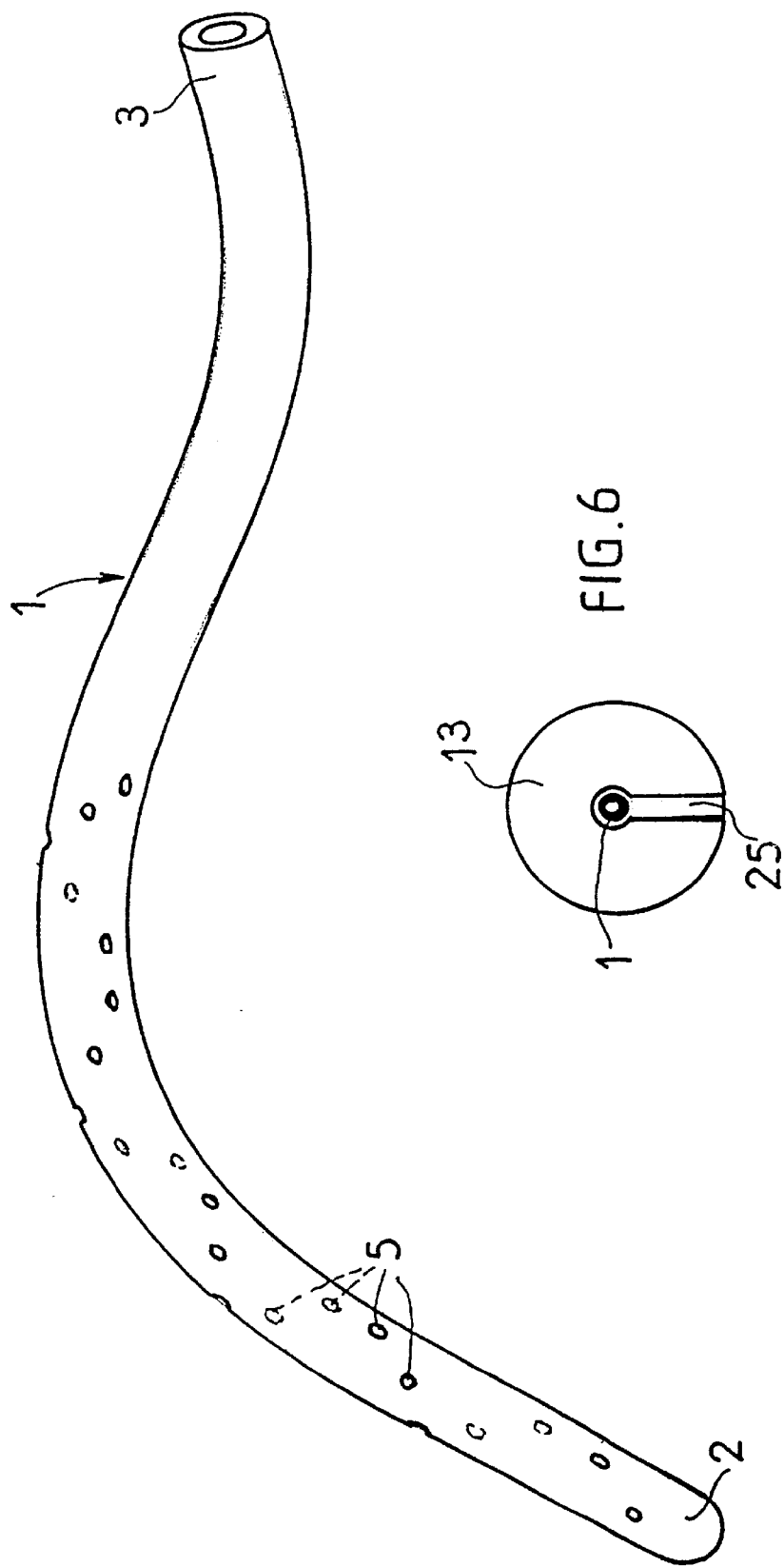

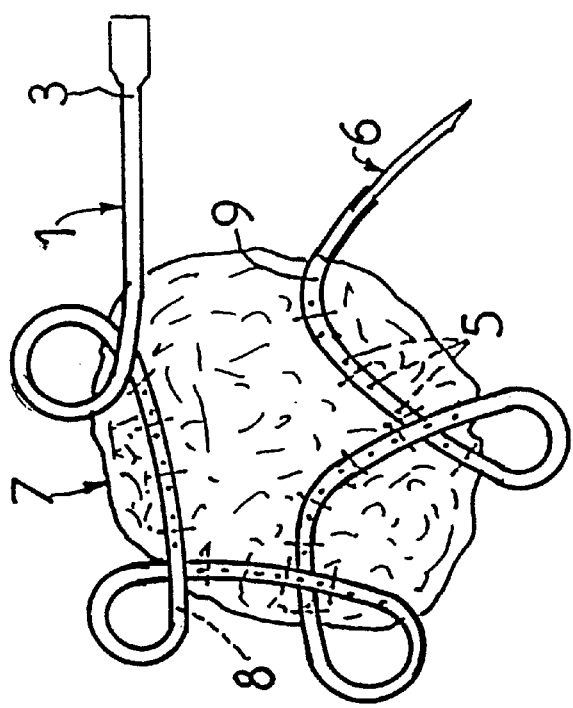
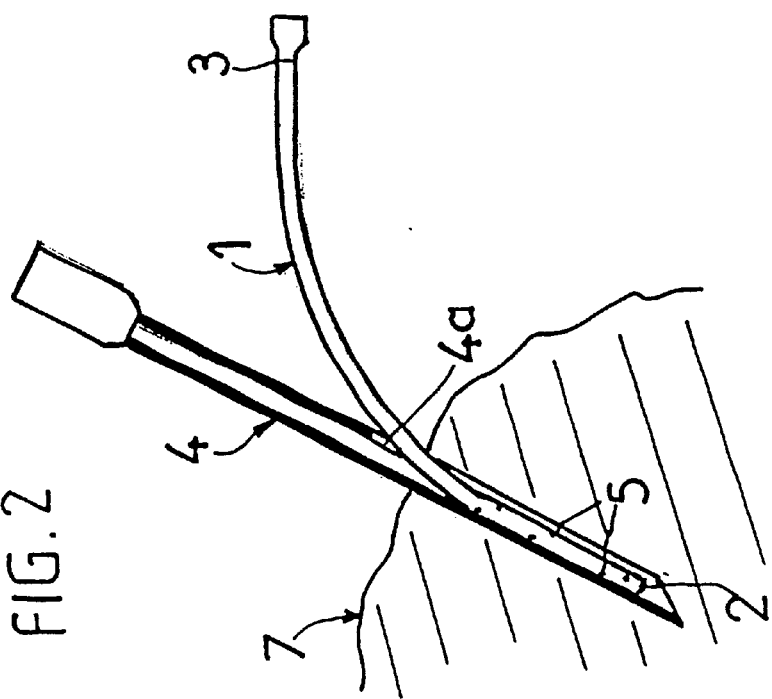

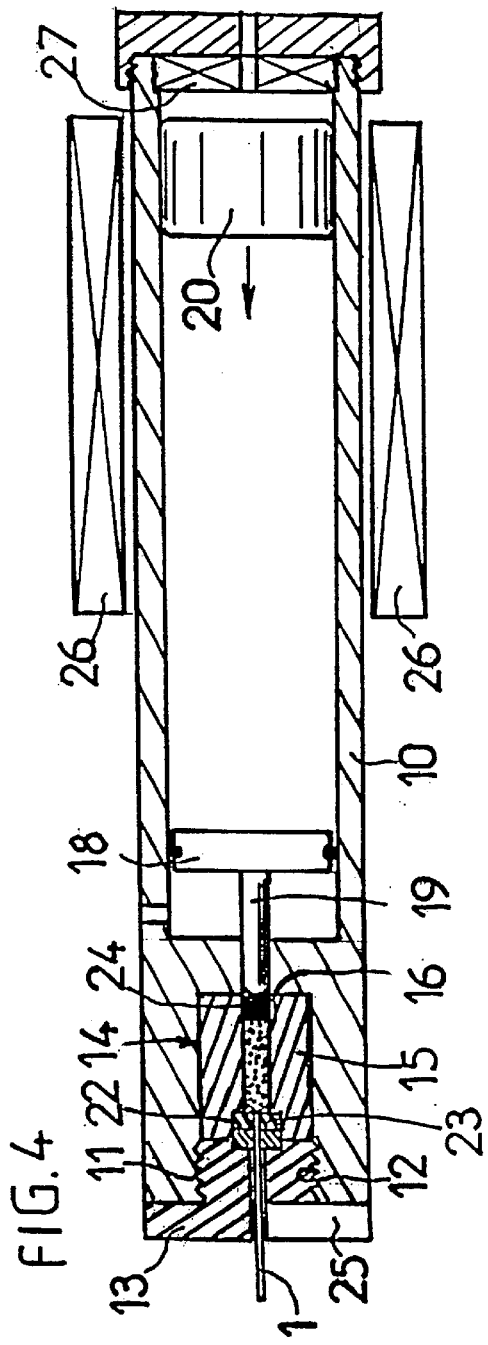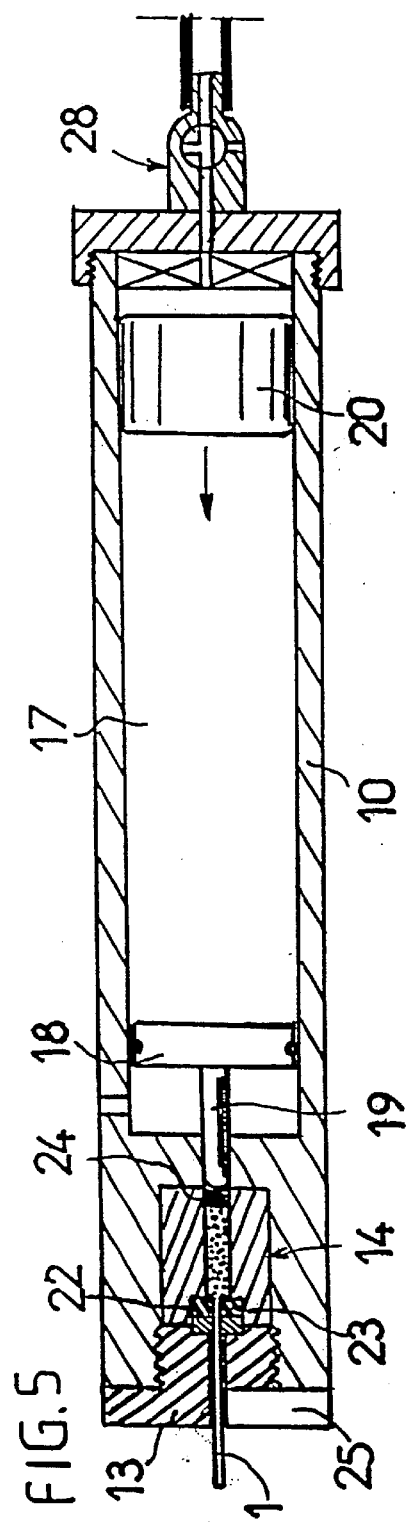

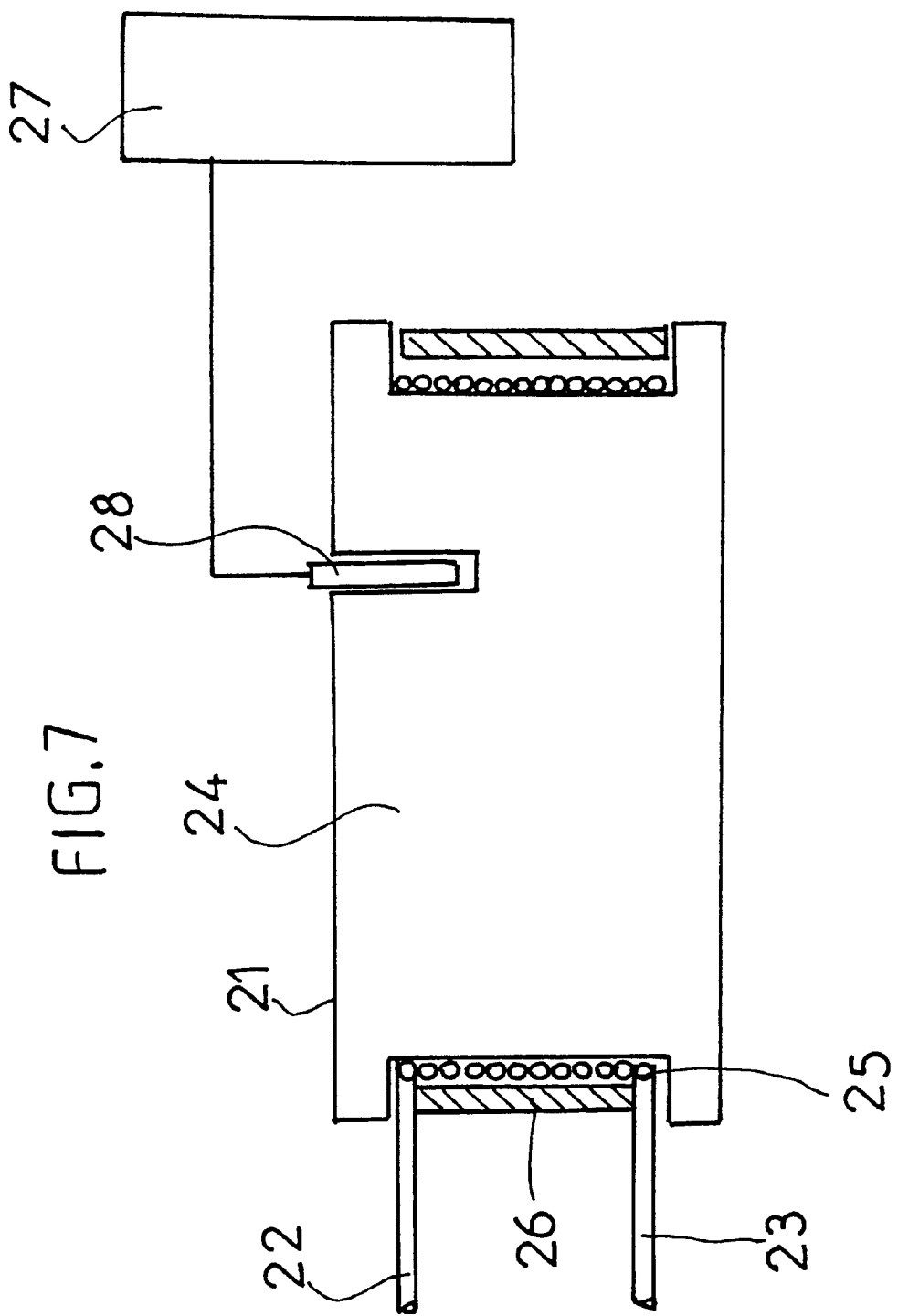

DEVICE FOR DIRECTLY DELIVERING AN ACTIVE SUBSTANCE WITHIN A CELL TISSUE, MEANS FOR IMPLANTING SAID DEVICE AND APPLIANCES FOR INJECTING ACTIVE SUBSTANCE INTO SAID DEVICE

CROSS REFERENCE TO RELATED APPLICATIONS

This application is a continuation of PCT application PCT/FR 99/02234 filed Sep. 21, 1999 designating the United States, and published in French as WO 00/29055 on May 25, 2000. PCT/FR99/02234 claimed the priority of French applications FR 98.14582 filed Nov. 17, 1998 and FR 99.03624 filed Mar. 19, 1999. The entire disclosures of all are incorporated herein by reference.

FIELD OF THE INVENTION

The invention relates to a device intended to deliver an active substance directly within all or some of a human or animal cell tissue. It also relates to the means of implanting this device within the tissue, and to the appliances intended for injecting active substance into said device.

In the remainder of the description and in the claims, the expression "active substance" will be used to denote any chemically or physically active substance and, more broadly speaking, any substance capable of being introduced into the organism whether for diagnostic, therapeutic or even cosmetic purposes.

Likewise, the expression "human or animal cell tissue" will be used to denote any organ or part of an organ.

BACKGROUND OF THE INVENTION

In the context of cancer treatments using ionizing radiation, there are a number of solutions which have been proposed with a view to concentrating the active principle in the cells of the patient that are to be treated while limiting the destruction of healthy cells.

Document WO 97/18011 has thus proposed an installation for concentrating an active principle associated with magnetic vectors in the cells of a patient that are to be treated. The installation employed is capable of creating a focused magnetic field gradient and then, by increasing the strength of the magnetic field, of causing the magnetic vectors to switch from the non-magnetized state to the magnetized state so as to cause a lasting aggregation thereof in the area of the cells that are to be treated.

However, even though this installation makes it possible to limit, or even to eliminate, the irradiation of healthy cells, it is nonetheless cumbersome to implement.

Also proposed, in document JPS Volume 71, number 4, April '82 (page 382) a method which consists in injecting, by an arterial route, an active principle associated with magnetic vectors subjected to an external magnetic field, which is then focused on the cells that are to be treated. However, it is found that a significant proportion of the magnetic vectors aggregate and remain trapped in the vessels of the circulatory system, thus irradiating a great many healthy cells.

Still in the context of cancer therapy, cancer cells are advantageously treated with heat, in addition to the conventional active principles, inasmuch as heat has an immediate cytolytic effect on said cells. In practice, the cancerous cells are heated up using a microwave treatment. This therapy thus makes it possible to raise the temperature in a localized way and thus give rise to hyperthermia.

Heat treatment is also employed for stopping hemorrhaging, particularly hemorrhaging likely to arise during surgical operations, and thus cause hemostasis. In practice, hemostasis is obtained by electro-coagulation by means of an electric lancet.

The problem of concentrating the active principle in the cells that are to be treated is not restricted to cancer treatments, but also relates to a good many other therapies whether these be chemotherapies, antibiotic therapies, etc.

Document U.S. Pat. No. 5,569,197 proposes concentrating an active principle via an endolumenal route at atheroma plaques formed on the internal walls of the arteries. The device employed corresponds to a tube made of a material said to be "superelastic" with outside diameter greater than 250 micrometers, advantageously 360 micrometers, and of which the walls at the distal end of said tube have perforations. Furthermore, the distal end of the tube is open and can be equipped with a filament which itself has an opening intended to deliver the active principle. The supple filament has the function of guiding the tube in the small vessels. The active principle, being in liquid form, is delivered exclusively to the atheroma plaques by infusion at a pressure not exceeding 4 atmospheres, that is to say slightly higher than 4 bar.

First of all, the device described in that document makes it possible to obtain a therapeutic effect only in vascularized organs, insofar as the device proposed is used exclusively by an endolumenal route. In addition, the active-principle concentration in the area to be treated is raised only temporarily, the remainder of the active principle diffusing through the organism.

In other words, the first problem that the invention sets out to solve is that of providing a device capable of delivering an active substance to any organ whatsoever.

A second problem that the invention sets out to solve, is that of providing a device capable of allowing a homogenous release of active substance in situ exclusively in all or some of the cell tissue that is to be treated, without any diffusion into the organism.

Another problem that the invention sets out to solve is that of providing a device capable of dispensing any type of active principle whether this be a chemical active principle or a physical active principle, and in any form whatsoever—liquid, solid or even vapor.

In order to do this, the present invention proposes a device capable of delivering an active substance directly within all or some of a human or animal cell tissue.

SUMMARY OF THE INVENTION

This device is characterized in that it is in the form of a hollow tube, of which the walls in contact with said tissue are equipped with at least one perforation, and of which the distal end is plugged, while the proximal end is shaped in such a way as to accommodate removable closure means, said tube being capable of withstanding a pressure of at least 50 bar.

In other words, the idea that the Applicant has had is to deliver an active principle not via an endolumenal route, but directly to the cell tissue by injecting said active principle into a target area at a high pressure of at least 50 bar, making it possible to obtain maximum effect, including into the thickness of the tissue.

Faced with this problem, the Applicant developed a device capable of withstanding a high pressure allowing the active principle to be injected directly into the tissues to a depth that varied according to the pressure used. Furthermore, and given the high pressure, the device can have active principles in liquid, solid or even vapor form passing through it.

In practice, the perforated walls of the hollow tube are positioned at the target organ to be treated, while the remainder of the tube connects to the outside of the organism, the tube thus remaining in position for the duration of the treatment. In consequence, the tube via its proximal end receives the active substance that it delivers via its perforations exclusively to the tissues that are to be treated.

As will be explained later, the active substance has to be given sufficient energy that it can be propelled through the perforations, then effectively penetrate the tissues that are to be treated.

At the same time, the tube must retain a certain suppleness to make it easier to install within the organism and, more particularly, at the tissues.

In order to satisfy these requirements, the choice of the diameter and of the thickness of the tube are the result of a compromise between said tube being supple, and its being able to withstand pressure and resist stretching.

When a chemically active substance is to be injected into the tissues, the pressure may reach 3 000 bar or even 10 000 bar if the desire is to inject a powder.

In a first embodiment, in order to withstand such a pressure while at the same time maintaining a certain suppleness, the outside diameter of the tube is between 100 and 250 micrometers, while the inside diameter of the tube is between 50 and 150 micrometers.

For an outside diameter greater than 250 micrometers, it is necessary to increase the thickness of the tube in order to withstand the pressure, which means that the flexibility disappears. By contrast, for an inside diameter smaller than 50 micrometers, the loss of energy of the active substance as it travels down the tube is too great, which means that the active substance cannot be propelled into the tissue that is to be treated.

Advantageously, the outside diameter of the tube is equal to 200 micrometers while the inside diameter of the tube is equal to 100 micrometers.

Likewise the perforations formed on the walls of the tube are substantially circular and have a diameter of between 30 and 70 micrometers, advantageously 50 micrometers. In practice, these perforations are made using a laser.

For a diameter smaller than 30 micrometers, the perforations are too small to allow the active substance to pass. On the other hand, for a diameter greater than 70 micrometers, the opening is too great for the tube to have satisfactory strength.

Furthermore, in order to withstand an internal pressure which may as high 10 000 bar, the material used to make the tube is chosen from the group comprising stainless steel and titanium. Thus, the radius of curvature of the tube obtained is of the order of 1 centimeter, this being without permanent deformation.

However, any material capable of withstanding high pressures of the order of 3 to 10 000 bar can be used.

Incidentally, in the case of the injection of a physically active substance, such as water vapor or alternatively hydrogen peroxide vapor, the pressure is at least 50 bar, and in practice is equal to 200 bar.

In addition, when using hydrogen peroxide by way of active principle, an additional therapeutic effect is achieved by the conversion of hydrogen peroxide, particularly into nascent oxygen.

Advantageously, use is made of an aqueous solution of hydrogen peroxide, the concentration of which is between 40 and 60% by volume.

In this case, given the lower pressure, the outside diameter of the tube may be higher without, however, the tube losing it suppleness.

In consequence, and according to a second embodiment, the outside diameter of the hollow tube is between 300 and 700 micrometers, while the inside diameter is between 100 and 300 micrometers.

For an outside diameter greater than 700 micrometers, it is necessary to increase the thickness of the tube in order to withstand the pressure, which means that the flexibility disappears. By contrast, for an outside diameter smaller than 100 micrometers, the loss in energy of the vapor as it travels along the tube is too great, which means that it cannot be propelled into the organ that is to be treated.

Furthermore, and according to this embodiment, the perforations formed on the walls are substantially circular and have a diameter of between 100 and 200 micrometers, advantageously of 150 micrometers.

For a diameter smaller than 100 micrometers, the perforations are too small to allow an effective amount of the vapor to pass. On the other hand, for a diameter greater than 200 micrometers, the opening is too large to allow the tube to have satisfactory strength.

In order to withstand a pressure in practice of the order of 200 bar, while at the same time maintaining maximum suppleness and resistance to heat, the tube is advantageously made of polytetrafluoroethylene (PTFE) or Teflon®. Of course, any material that is equivalent in terms of ability to withstand pressure may be envisioned.

Although water vapor or hydrogen peroxide vapor can be injected into a tube with the above-described properties, they can also be injected into a tube identical to the one used for injecting a chemical active principle, at a lower pressure, of the order of 200 bar. In such a case, the medic will have just one device that he will be able to use in situ to administer either chemical active principle or physical active principle in the form of vapor.

According to this embodiment, the part of the tube which is not in contact with the tissue that is to be treated is sheathed with an insulating material which is supple and resistant to heat.

In order to achieve a homogenous distribution of active principle, the perforations are formed in a spiral around the part of the tube that is intended to be in contact with the organ that is to be treated, with a pitch of between 0.1 and 2 centimeters.

Furthermore, as already stated, the proximal end of the tube has removable closure means. In practice, but without implying any limitation, these means may be in the form of a threaded plug intended to collaborate with a corresponding tapping made in the proximal end of the tube.

In addition, in order to participate in the connection between the tube and the appliance intended for injecting active substance, which appliance is described hereinafter, said tube has a conical seal fixed near its proximal end.

As already stated, use of the device of the invention is not restricted to oncology but also relates to antibiotic therapy. In this context, the tube of the invention finds a particularly advantageous application in orthopedics. What happens is that surgical implantation of a prosthesis may give rise to an infection which is often difficult to treat locally. In such an instance, the surgeon may implant an osteosynthesis element such as a prosthesis, a nail, etc, equipped by any known means with the hollow tube of the invention, which will remain in communication with the surroundings external to the organism.

By way of example, the microtube may be lodged in a spiral-cut groove made in the surface of the material implanted in the bone. In this case, the active principle injected may be an antibiotic, in the event of bone infection, or a sealant in the event of a prosthesis working loose.

The invention therefore also relates to an osteosynthesis element equipped with the tube of the invention.

The invention is also aimed at a means of implanting the above-described device within a target human or animal organ. This implantation may be performed in various ways.

According to a first method, the tube is implanted by image-guided puncturing using a needle. In this case, the implantation means is therefore in the form of a needle intended to accommodate the tube, said needle having, over all or part of its length, a slot so that the tube can be freed and held in position after the needle has been withdrawn.

According to another method, implantation is performed surgically. In this case, the implantation means is in the form of a needle fixed to the distal end of the hollow tube, the fixing being achieved by any known means.

According to this technique, if there is a desire for said tube to be implanted around a target organ, for example the liver, perforations are then made on lengths of tube equal to the length of the needle, these being separated by unperforated lengths, which may be identified in particular by deposits of gold for needle takeup, the unperforated lengths thus lying outside of the organ that is to be treated.

According to another method, implantation is performed by an endovascular route, the tube then constituting the catheter.

The invention also relates to the appliance intended for injecting active substance into the device.

However, the configuration of the appliance may vary according to the pressure at which the active substance is injected.

Thus, when the active substance is injected at very high pressure, of the order of 3 to 10 000 bar, the appliance is characterized in that it has:
  on the one hand, a means of storing the active principle which can be connected to the proximal end of the tube;
  and, on the other hand, means capable of allowing the active substance to be injected through the tube.

In practice, the proximal end of the tube outside the organism is connected directly to the storage means which is subjected to means which will allow the active substance to be injected into the tube at a pressure such that it will be propelled through the perforations so that it reaches the target area that is to be treated.

According to a first embodiment, the means of storing the active substance is in the form of a cylinder, the central axis of which is hollowed out to form a cylindrical reservoir intended to contain the active substance, and one of the ends of which is intended to be connected directly to the proximal end of the tube, while the other end is plugged by a sealed plug that can move axially inside the cylindrical reservoir under the effect of the rod of a piston.

At the same time, and according to another feature of the appliance, the means capable of allowing the active principle to be injected into the tube are in the form of a mass intended to be thrown against the piston, which will act via its rod on the sealed moving plug thus causing active substance to be ejected into the tube.

In another embodiment, the active substance is stored in a deformable-walled ampoule which is positioned in the abovementioned cylindrical reservoir, the end of the ampoule being connected by any known means to the proximal end of the tube. This embodiment thus makes it possible to have doses of active substance available ready for use.

Incidentally, the mass may be propelled by various means, particularly by means of a pneumatic system or alternatively of an electromagnetic system.

Moreover, when the active substance is a physically active substance, particularly water vapor or hydrogen peroxide vapor, the appliance is characterized in that it is has:
  a means of heating the active substance,
  a means of conveying the active substance to the heating means,
  a means of transmitting the heated active substance into the tube.

As already stated, the physically active substance employed is, in practice, in the form of water vapor or hydrogen peroxide vapor.

In practice, the means of conveying the active substance and the means of transmitting the heated active substance to the tube of the invention are in the form of a stainless steel tube wound around an aluminum reel.

In addition, the active substance heating means is in the form of a resistive electric element wrapped around the reel-tube assembly.

According to another feature, the reel is equipped with a platinum probe connected to the electric system thus allowing the temperature to be regulated.

In practice, the water or the hydrogen peroxide is injected into the stainless steel tube at a minimum pressure of 200 bar and emerges via the same stainless steel tube after having been heated by the reel to a temperature close to 400° C.

The invention finally relates to a method of administering an active substance directly within all or some of a human or animal tissue according to which:
  first of all, the tissue that is to be treated is located,
  a hollow tube, the walls of which are intended to be in contact with the tissue that is to be treated are equipped with at least one perforation, and the distal end of which is plugged is then introduced into the organism as far as said tissue, the proximal end of said tube connecting to the outside of the organism,
  next, the active substance is injected under a pressure of at least 50 bar into said tube so that it is delivered to the tissues via the perforations,
  the proximal end of the tube is finally plugged,
  at the end of the treatment, the tube is withdrawn.

As already stated, the hollow tube can be introduced into the organism by any known means and particularly using the implantation means described hereinabove.

Likewise, active substance is injected using an appliance of the type already described or any equivalent means, the appliance being detached from the tube after each injection.

Of course, the same tube can be used, as desired, to inject a chemical or physical active substance. In practice, the surgeon may, when implanting the tube, give rise to hemostasis, if need be, by injecting vapor.

Furthermore, the active substance may adopt different forms, particularly liquid or alternatively solid, for example in the form of nanocapsules, nanoparticles or microparticles.

It is thus possible to envisage all types of active substance, whether these be those used in chemotherapy or alternatively in antibiotic therapy, and antiinflammatories and radioactive products for therapeutic use, these being mentioned without any implied limitation.

In one advantageous embodiment, the active substance may be associated with magnetic nanoparticles of ferrite of a size between 100 and 1 000 nanometers.

It then follows that when the active substance is being injected through the tube, the energy imparted to the magnetic nanoparticles means that they behave independently of one another, their mutual magnetic attraction effectively becoming negligible by comparison with their kinetic energy. By contrast, after injection, that is to say in situ, the magnetic attraction encourages the nanoparticles to group together again in the form of clumps measuring about 50 micrometers, in the organ or the area of the organ that is to be treated.

In the case of a radioactive active principle, said radioactive active principle may adopt two different forms:

it may either consist of radioactive isotopes grafted onto magnetic particles;

or it may be included in the magnetic particle and may consist of radioactive isotopes of the magnetic elements that make up the magnetic particles.

Advantageously, the radioactive product may be an emitter of $\alpha$, $\beta$ and $\gamma$ radiation for therapeutic purposes, preferably at low energy, so as to obtain the most localized possible irradiation. It may also be beneficial to combine a $\gamma$-emitter of an energy between 100 and 150 kiloelectron-volts (keV) or $\beta+$ emitter in order that the location of the nanoparticles can be viewed using a $\gamma$-camera. This also makes it easier to calculate the radiation dose.

As already stated, nanoparticles of ferrite may be used by way of magnetic particles.

In such a case, the stable product yielding the radioactive product by irradiation with neutrons or charged particles is incorporated during the manufacture of ferrite nanoparticles, the components of the ferrite yielding, following irradiation, parasitic radioactive products of very short half-life which therefore decay very quickly. Thus, only the radioactivity of the chosen therapeutic radioactive element remains.

In another form of embodiment, an active substance can be combined with liquid mercury (Hg) or mercury in an amalgam in the form of nanoparticles. What happens is that at the time of injection, the liquid mercury adopts the micro-droplet form, the kinetic energy of which is high because of its high density. In situ, that is to say in the organ, the high surface tension of the mercury encourages the microdroplets to group together into larger beads thus fixing the active substance in the organ that is to be treated.

In addition, mercury has a radioactive isotope (Hg 197) well suited to therapy. Thus, the active principle Hg 197 is included in the mercury nanoparticles. Furthermore and as already stated, mercury produces amalgams with most metals, which therefore makes it possible to fix other metallic radioactive products in the form of traces, the mercury remaining liquid.

BRIEF DESCRIPTIONS OF THE DRAWINGS

The advantages of the invention will become clearly apparent from the exemplary embodiment hereinafter in support of the appended figures.

FIG. 1 is a depiction of the device of the invention.

FIG. 2 is a depiction of a first implantation means.

FIG. 3 is a depiction of a second implantation means.

FIG. 4 is a depiction of an appliance intended to inject the active principle into the tube when said active principle is injected under very high pressure of the order of 3 000 to 10 000 bar.

FIG. 5 is a depiction of an appliance of the same type as the one in FIG. 4 according to another form of embodiment.

FIG. 6 is a depiction of FIG. 5 along the axis II.

FIG. 7 is a depiction in section of an appliance intended for injecting active principle when said active principle is injected at a pressure of the order of 200 bar.

DETAILED DESCRIPTIONS OF THE DRAWINGS

FIG. 1 depicts the hollow tube that is the subject of the invention denoted by the general reference 1. The hollow tube has a plugged distal end (2) while the proximal end (3) is shaped in such a way as to accommodate a removable closure means, for example a plug. In practice, the proximal end of the tube has a tapping (not depicted) intended to collaborate, by screwing, with the screw thread of the plug.

The diameter varies according to the pressure to which it is subjected. Thus, if the pressure is of the order of 3 000 bar and over, the outside diameter of the tube is 200 micrometers, while its inside diameter is chosen to be equal to 100 micrometers. If the pressure is of the order of 200 bar, the outside diameter is 400 micrometers while its inside diameter is chosen to be equal to 150 micrometers. Of course, the length of the tube varies according to the distance between the point of introduction of the tube into the organism and the organ that is to be treated.

Furthermore, in order to allow the active principle to be made available homogeneously, the tube has perforations (5) produced using a laser in a spiral on the part of the tube that is intended to be in direct contact with the tissue to be treated, this being with a pitch equal to 0.5 centimeters for example.

In addition, in order to make the tube easier to connect to the injection appliances described hereinafter, the tube near its proximal end has a frustoconical seal. It is pierced at its center with an orifice corresponding to the diameter of the tube.

In order for the tube to maintain its entire suppleness and to be able to withstand the high pressure, it is made of stainless steel of grade A304 (international standard).

FIG. 2 depicts a first means of implanting the tube within an organ.

In this embodiment, implantation is achieved by guided puncturing using a needle (4). The needle is intended to accommodate the tube and over all or part of its length has a slot (4a) for freeing the tube and holding it in position once the needle has been withdrawn. FIG. 2 also illustrates a removable closure means (30), for example, a plug, for instance, a threaded plug, which threads into a corresponding tapping in the proximal end (3) of the tube (1). In one aspect of the invention, removable closure means (30) may comprise a seal, for example, a conical seal, which may be fixed to the proximal end (3).

According to another embodiment, shown in FIG. 3, the implantation means is in the form of a needle (6) arranged at the distal end (2) of the tube (1) by any known means, particularly by crimping. The tube is thus "sewn" all around the member (7) that is to be treated. In this case, and in order to release active substance exclusively in the organ, the perforations are formed only on both parts (9) which are in contact with the organ, the parts (8) of the tube remaining outside the organ and being plugged, thus preventing active substance from being released in these regions. FIG. 3 also illustrates a removable closure means (31), which may be similar to removable closure means (30) shown in FIG. 2, according to another aspect of the invention.

FIG. 4 depicts the first embodiment of an appliance intended for injecting active substance into the tube (1) under high pressure of the order of 3 000 bar and over. This appliance is in the general form of a cylinder (10). This cylinder is equipped at one of its ends with a tapping (11) intended to collaborate with the screw thread (12) of a screw (13). The appliance of cylindrical shape (10) also has two compartments:

- a first compartment (14) located near the plug (13) and intended to accommodate a cylinder (15) constituting the means of storing the active substance, the central axis of which is hollowed out so as to form a cylindrical reservoir (16) intended to contain the active substance proper;
- a hollow cylindrical second compartment (17) forming a chamber in which a piston (18) equipped with a rod (19) is moved in terms of translation under the action of a mass (20).

At its end adjacent to the plug (13) the cylinder (15) also has a recess (22) intended to house a washer, particularly an elastomer washer (23). At its opposite end, the cylinder (15) has a plug (24) intended to plug the cylindrical reservoir (16).

As depicted in that same figure, the plug (13) is pierced right through along its central axis, so as to allow the passage of the tube (1). To simplify fitting of the tube (1) through the plug (13), the latter longitudinally has a radial slot (25) (see FIG. 6).

As already stated, the chamber (17) contains a mass (20) intended to be thrown against the piston (18). The mass (20) is kept stationary by means of a magnet (27) positioned in the end of the compartment (17). The mass (20) may be propelled in various ways.

A first way consists in creating a magnetic field using a winding (26).

The mass may also be propelled by means of a compressed-air system (28) as depicted in FIG. 5.

FIG. 7 depicts an appliance intended for injecting active substance under a pressure of the order of 200 bar. As already stated, in this case, the substance injected is a physically active substance, particularly in the form of water vapor or hydrogen peroxide vapor.

According to this embodiment, the appliance has:

- a means (21) of heating the water or the hydrogen peroxide;
- a means (22) of conveying the water or hydrogen peroxide;
- and a means (23) of transmitting the vaporized water or hydrogen peroxide.

The means of conveying water or hydrogen peroxide and the means of transmitting the vaporized water or hydrogen peroxide are in the form of an aluminum reel (24) of a diameter equal to 100 millimeters and of a height equal to 60 millimeters, wound with a stainless steel tube (25) of an outside diameter of 1.6 millimeters and of an inside diameter of 0.3 millimeters, of a length of between 1,500 and 3 000 millimeters. The end (22) of the tube (25) corresponds to the means of conveying the active substance and the end (23) corresponds to the means of transmitting the vapor to the tube of the invention.

The assembly comprising reel (24) and stainless steel tube (25) has an actual heating means proper in the form of an electric resistive element (26) wrapped around it.

Furthermore, the reel (24) is fitted with a probe (28) connected to the electrical power supply (27) which regulates the temperature of the reel.

In practice and as already stated, water is injected at a pressure of 200 bar into the stainless steel tube, the water then being heated by means of the reel to a temperature of 400° C., corresponding to a vapor saturation tension of 200 bar, the vapor being reinjected into the tube that is the subject of the invention at a pressure of 200 bar.

In practice, the surgeon will first of all delimit the tissue or the part of the tissue that is to be treated, and therefore its position. He thus determines the length of the tube needed to reach said tissue from the point of introduction of the tube into the organism. At the same time, he chooses the appropriate tube, that is to say the one which has perforations positioned in such a way that the active substance is released exclusively into the tissue or part of the tissue that is to be treated. He then positions the tube at the organ that is to be treated, either by guided puncturing or surgically using a needle, or alternatively by an endovascular route. The length of the tube is chosen so that only a short length, of the order of about ten centimeters, remains outside the organism. The proximal end of said tube is then connected to the appliances described hereinabove.

As far as the first of these two appliances is concerned, the tube is introduced into the radial slot formed in the plug of the appliance. The tube is then connected to the cavity containing the active substance by screwing the plug in, which leads to close contact between the steel washer and the elastomer washer.

Once the tube has been connected to the storage means, the mass is thrown against the piston so that the active substance is injected directly into the tube and delivered exclusively to the organ that is to be treated.

As far as the second appliance is concerned, the tube of the invention is connected directly to the end of the stainless steel tube by any known means.

Of course, and as already stated, the tube may remained positioned at the organ throughout the duration of the treatment. In this case, after each injection of active substance, the tube is sealed again. At the end of treatment, the tube will be withdrawn.

The advantages of the invention are clearly apparent from the description. The simplicity of the hardware used and the effectiveness of the treatment in sofaras the active substance can be administered in situ exclusively in the area that is to be treated and deeply within it are of particular note.

What is claimed is:

1. A device for directly delivering an active substance from an exterior source to within human or animal cell tissue, the device comprising a hollow tube substantially circular in cross-section having a proximal end, a distal end, an interior surface defining an inside diameter and a smooth exterior surface made of a contiguous material from the proximal end to the distal end, defining an outside diameter;
    (a) said exterior surface defining an outside diameter between 100 and 250 micrometers;
    (b) said interior surface defining an inside diameter between 50 and 150 micrometers;
    (c) said exterior surface and said interior surface being in fluid communication via a plurality of perforations having diameters between 30 and 70 micrometers;
    (d) said distal tube end being closed; and
    (e) said proximal tube end communicating with the exterior source of active substance,
    wherein said hollow tube is capable of withstanding high pressure delivery of at least 50 bar.

2. The device of claim 1 wherein said proximal tube end communicates with said exterior source of active substance via a removable closure.

3. The device of claim 2 wherein said removable closure comprises a tapping for a threaded seal.

4. The device of claim 1 further comprising a conical seal fixed to said proximal end.

5. The device of claim 1 wherein said exterior source of active substance is at 50 to 10,000 bar.

6. The device of claim 1 wherein said device is made from a material chosen from stainless steel, titanium and polytetrafluoroethylene.

7. The device of claim 1 wherein said perforations are formed in a spiral with a pitch of between 0.5 and 2 centimeters.

8. The device of claim 1, wherein at least some of the exterior surface of the device contacts the tissue.

9. The device of claim 1, wherein the inside diameter of the tube is uniform.

10. A method for delivering an active substance directly within a tissue comprising:
   (a) inserting a device according to claim 1 into or adjacent said tissue; and
   (b) applying said active substance to said tissue by forcing said active substance under pressure through said device and into said tissue.

11. A method according to claim 10 wherein said pressure is 50 to 10,000 bars.

12. A method according to claim 10 wherein said active substance is one or more members chosen from the group consisting of hydrogen peroxide vapor, water vapor, an antibiotic, a chemotherapeutic agent, an anti-inflammatory agent, a radioactive therapeutic agent and a metallic particle.

13. A method according to claim 10 wherein said tissue is liver or bone.

* * * * *